(12) United States Patent
Lu et al.

(10) Patent No.: US 9,689,017 B2
(45) Date of Patent: Jun. 27, 2017

(54) **METHOD OF SEMI-SOLID STATE FERMENTATION FOR PRODUCING SURFACTIN FROM A MUTANT STRAIN OF *BACILLUS SUBTILIS* SUBSP**

(71) Applicants: SAFT biotechnology com. LTD, Nanjing (CN); Jenn-Kan Lu, New Taipei (TW)

(72) Inventors: Jenn-Kan Lu, New Taipei (TW); Yi-Peng Lin, Taipei (TW); Hsin-Mei Wang, Pingtung (TW)

(73) Assignees: Saft Biotechnology Com. Ltd., Nanjing (CN); Jenn-Kan Lu, New Taipei (TW)

(*) Notice: Subject to any disclaimer, the term of this patent is extended or adjusted under 35 U.S.C. 154(b) by 0 days.

(21) Appl. No.: 14/955,444

(22) Filed: Dec. 1, 2015

(65) Prior Publication Data

US 2016/0237467 A1 Aug. 18, 2016

(30) Foreign Application Priority Data

Dec. 1, 2014 (TW) .............................. 103141552 A

(51) Int. Cl.
| | | |
|---|---|---|
| *C07K 14/32* | (2006.01) | |
| *C12P 21/02* | (2006.01) | |
| *C12R 1/125* | (2006.01) | |
| *C12N 1/20* | (2006.01) | |

(52) U.S. Cl.
CPC .............. *C12P 21/02* (2013.01); *C07K 14/32* (2013.01); *C12N 1/20* (2013.01); *C12R 1/125* (2013.01); *Y02P 20/582* (2015.11)

(58) Field of Classification Search
None
See application file for complete search history.

(56) References Cited

U.S. PATENT DOCUMENTS

| | | | | |
|---|---|---|---|---|
| 5,227,294 A * | 7/1993 | Carrera | ..................... | C07K 7/06 435/252.31 |
| 5,264,363 A * | 11/1993 | Carrera | ..................... | C07K 7/06 435/252.31 |
| 9,364,413 B2 * | 6/2016 | Lu | ........................... | A61K 8/64 |
| 2004/0043451 A1* | 3/2004 | Yoneda | .................. | C07K 14/32 435/69.1 |
| 2010/0093060 A1* | 4/2010 | Jarrell | ...................... | C12N 1/20 435/252.5 |
| 2011/0059487 A1* | 3/2011 | Jarrell | ...................... | C12N 1/20 435/69.1 |
| 2015/0045290 A1* | 2/2015 | Coutte | .................. | C07K 14/32 514/3.6 |
| 2016/0030324 A1* | 2/2016 | Lu | .......................... | A61K 8/64 424/649 |
| 2016/0183556 A1* | 6/2016 | Lu | ........................ | A23K 1/007 424/116 |

FOREIGN PATENT DOCUMENTS

CN 103865855 * 3/2014

OTHER PUBLICATIONS

Capalbo D. Bacillus thuringiensis: Fermentation Process and Risk Assessment. Mem Inst Oswaldo Cruz 90(1)135-8, Jan.-Feb. 1995.*
Ohno A. et al. Production of a Lipopeptide Antibiotic, Surfactin, by Recombinant Bacillus subtilis in Solid State Fermentation. Biotech Bioengineering 47(2)209-214, 1995.*
Shaligram N. et al. Surfactin—A Review on Biosynthesis, Fermentation, Purification and Applications. Food Techol Biotechol 48(2)119-134, 2010.*
Nakayama S. et al. Isolation of a New Variants of Surfactin by a Recombinant Bacillus subtilis. Appl Microbiol Biotechnol 48(1)80-82, Jul. 1997.*
Hai P. et al. Optimization of Semi-Solid Fermentation Conditions for Highest Protease Activity from Bacillus subtilis. World Aquaculture Society, Meeting Dec. 11, 2013.*
Peypoux F et al. Recent Trends in the Biochemistry of Surfactin. Appl Microbiol Biotechnol 51(5)553-563, May 1999.*

* cited by examiner

*Primary Examiner* — Ralph Gitomer
(74) *Attorney, Agent, or Firm* — Muncy, Geissler, Olds & Lowe, P.C.

(57) ABSTRACT

Surfactin is produced from *Bacillus subtilis* ssp. containing sfp gene (lipopeptide biosurfactants produced by fermentation). Production of surfactin at present is mainly by liquid fermentation, but the production costs are high due to difficulty in purification resulted from addition of the defoaming agent during the production process. Therefore, present invention conducts physical or chemical mutation on *Bacillus subtilis* subsp. isolated from Thailand seawater shrimp ponds and screens for the mutant strain of *Bacillus subtilis* subsp. based on sfp gene expression and then produces surfactin from the mutant strain by semi-solid state fermentation.

10 Claims, 6 Drawing Sheets

METHOD OF SEMI-SOLID STATE FERMENTATION FOR PRODUCING SURFACTIN FROM A MUTANT STRAIN OF BACILLUS SUBTILIS SUBSP

BACKGROUND OF THE INVENTION

1. Field of the Invention

Present invention relates to a method of semi-solid state fermentation for production of surfactin from a high-yield mutant strain of *Bacillus subtilis* subsp.

2. Description of the Prior Art

Biosurfactants are secondary metabolites that are produced by microorganisms under certain conditions and contain both hydrophilic and hydrophobic structures. In addition to having the same or similar physical and chemical properties as the chemically synthesized surfactants, biosurfactants also have a number of other characters such as complex structure, high specificity, low toxicity, biodegradable, environmental friendly and can be produced by fermentation of cheap agricultural by-products. Moreover, certain biosurfactants also have antibacterial, anti-viral and anti-tumor pharmacological effects. Most lipopeptide biosurfactants (LPBSs) have anti-microbial effect and are also called antibiotics. At present, the major LPBSs identified include surfactin, fengycin, iturin, bacillomycin, mycosubtilin and plipstatin, etc. By far, biosurfactants have been widely used in the fields of cosmetics, food, oil and pharmaceutical industry.

In 1968, Arima et. al discovered a lipopeptide biosurfactant produced by *Bacillus subtilis* ssp. with high activity and named it surfactin. The yield of surfactin produced by Arimaet. al was only 0.04-0.05 g/L. In 1981, Cooper et. al used a basal mineral salt medium to grow *Bacillus subtilis* ATCC21332 and collected the foam and isolated surfactin, the yield was 0.78 g/L, Mulligan et. al in 1989 found a UV-induced mutant strain of *Bacillus subtilis* ATCC51338 and its surfactin yield was 1.124 g/L. In 1997, Kim et. al cultured *Bacillus subtilis* C9 under a condition with limited oxygen in an improved Cooper medium and its surfactin yield was 7.0 g/L. By 2000, Wei Yu-Hong et. al increased the yield of surfactin to 3.5 g/L by using a mineral enhanced salt medium and controlling the pH.

The main method for producing surfactin from *Bacillus subtilis* at present is liquid fermentation because the fermentation parameters that can be controlled are relatively more for liquid fermentation; nonetheless, the major controlling parameters are the ingredients of the media, exploration of fermentation conditions and screening of the high-yield strain. Studies have indicated that different carbon sources in the media indeed will affect the yield of surfactin (Lang, et al., 1999; Wei, et al., 2004; Wei, et al., 2005). Glucose can be used as the carbon source and be utilized by *Bacillus subtilis*; yet, excess glucose will result in reduced pH which then leads to reduced yield of surfactin. Therefore, production of surfactin is closely related to the pH of the media (Yeh, et al., 2005). Addition of long-chain carbon also helps increase the yield of surfactin (Ghribi and Ellouze-Chaabouni, 2011). Different nitrogen sources have two effects: 1. yield: adjusting the formula of the medium proposed by Cooper in 1981 by changing its nitrogen source and growing the bacteria under the anaerobic condition increases the yield of surfactin to 7 g/L (Kim, et al., 1997); 2. the structure of surfactin: addition of different hydrophobic amino acids to the medium changes the structure of surfactin (Peypoux, et al., 1992). When the concentrations of divalent and trivalent iron in the medium are increased from µg to mg, the total yield of surfactin produced by *Bacillus subtilis* ATCC 21332 will increase. On the other hand, addition of iron ions will lead to reduced pH of the medium and *Bacillus subtilis* will stop producing surfactin when the pH is lower than 5. Hence, addition of iron ions must be coordinated with adjustment of pH in order to facilitate surfactin production (Wei and Chu, 1998; Wei and Chu, 1998).

Moreover, addition of manganese ions to the media can significantly increase the yield of surfactin while not affecting the growth of *Bacillus subtilis* (Wei and Chu, 2002). Furthermore, growing *Bacillus subtilis* in a medium without metal ions of magnesium, potassium, manganese and iron was found to significantly decrease the yield of surfactin as well as the rate of growth, indicating the four ions are essential for the culturing process in spite of the fact that they are trace elements (Wei, et al., 2007). Some researchers pointed out, in addition to the ingredients of media, addition of solid carriers to media can also effectively increase the yield of surfactin. Because activated carbon is not easily degraded during the process of fermentation and can be easily dissociated from a medium, using activated carbon as the carrier to increase the number of cells so as to delay the cells from entering the stagnation stage can improve the yield of surfactin (Yeh, et al., 2005).

The disadvantage of liquid fermentation is that addition of a defoaming agent during the process of fermentation is required, which consequently leads to difficulties in purification. Thus, the method of fermentation needs to be changed in order to increase the yield of surfactin.

Except for liquid fermentation, other available methods include solid-state fermentation which is one important fermentation method in the fermentation industry due to low costs of its substrates. Previous literatures indicated the groups with low solid contents after fermentation of *Bacillus subtilis* subsp ATCC 21332 by using the waste generated from potato processing have higher yields of surfactin when compared with the groups with high solid contents (Nitschke, et al., 2004). Fermentation of the by-product and wastes of tofu processing by using *Bacillus subtilis* subsp MI113 at 37° C. for 48 hrs produces 2 g/kg of surfactin (Ohno, et al., 1995) and the surfactin produced from soybean fermentation using *Bacillus polyfermenticus* KJS-2 shows anti-microbial activity and its minimum inhibitory concentration (MIC) is 0.05 mg/mL (Kim, et al., 2009).

The disadvantages of solid-state fermentation include: 1. low water content limits the transmission rate of substances and energy and the heat generated during fermentation cannot be easily removed and thus resulting in a gradient of nutrition which then causes unbalanced fermentation; 2. fermentation parameters are not easily detected (e.g. pH value and biomass), poor reproducibility; 3. substrate stirring is not easy which may easily cause destroyed environment for microbial growth; 4. the time of solid-state fermentation is longer than liquid fermentation. Surfactin is one of the most active biosurfactants and has attracted much attention since its discovery. However, due to its low yield and high product costs, industrial application of lipopeptide biosurfactants have been unsuccessful. By far, large-scale industrial production of surfactin is still impossible. Hence, many inventors have devoted themselves to increasing the yield of surfactin. Moreover, transformation from laboratory techniques to industrial production is a very difficult issue due to instability of the bio-fermentation process.

How to reduce the production costs is the main goal of this study, which requires selection and culturing the high-yield strain as well as suitable and cheap culture media in order to reduce the fermentation costs and increase the unit yield. In addition, recycling of the fermented substrates and developing high value-added products are just the technical issues this study intends to address.

The purpose of the invention is to overcome the deficiencies of prior art and to provide a commercial preparation method for producing lipopeptide biosurfactants. This method adopts semi-solid state fermentation to improve part of the disadvantages of solid-state fermentation. Because the water content in semi-solid state fermentation is higher than that of solid-state fermentation, the problems of transmission rate of substances and energy, heat generated during fermentation and longer fermentation time can all be solved. Moreover, the yield of surfactin by semi-solid state fermentation can be increased by changing the basic conditions for fermentation such as water content, substrates for fermentation, and addition of oils as well as amino acids to supplement the carbon and nitrogen sources. This production technology offers high yield, high efficiency, short fermentation cycle and easy manufacturing process which can significantly reduce the production costs and is suitable for industrial application as well as large-scale production; moreover, it is very helpful for promotion and application of lipopeptide biosurfactants.

SUMMARY OF THE INVENTION

In one aspect, present invention provides a method of semi-solid state fermentation for producing surfactin from a mutant strain of *Bacillus subtilis* subsp.

Said method comprise the following steps:

Step 1: inoculation of *Bacillus subtilis* ssp. to a nutrient broth to give an activated bacterial culture; wherein the nutrient broth is consisting of peptone A at 5.0 g/L, NaCl at 5.0 g/L, beef extract at 1.5 g/L and yeast extract at 1.5 g/L and the pH is 7.4±0.2.

Step 2: treating the activated bacterial culture with either a physical or a chemical method to generate a mutant strain; wherein the physical method is to use UV light with a wavelength of 254 nm, 3,500-4,500 μW/cm2 to treat the culture for 1-50 seconds, and the chemical method is to use 15-20 μg/ml of EtBr to treat the culture at 25-30° C. for 20-28 hrs.

Step 3: inoculation of the mixed bacterial culture onto a solid nutrient agar and incubate at 25-30° C. for 12-20 hrs before selecting a single colony; wherein the solid nutrient agar is consisting of 0.5% peptone A, 0.3% beef extract, 0.3% yeast extract, 0.5% NaCl and 1.5% agar, and its pH is 6.8.

Step 4: inoculation of the single colony to a mineral salt medium and incubate at 25-30° C. for 20-28 hrs, followed by screening for the mutant strain with high yield; wherein the mutant strain is the strain with higher sfp expression. The higher the sfp expression, the higher the surfactin production. The mineral salt medium consists of 2-6% (v/v) glucose, 35-45 mM $Na_2HPO_4$, 25-35 mM $KH_2PO_4$, 45-55 mM $NH_4NO_3$, 5-10 mM $CaCl_2$, 2-6 mM Sodium EDTA, 750-850 mM $MgSO_4 \cdot 7H_2O$ and 1-3 mM $FeSO_4 \cdot 7H_2O$.

Step 5: inoculation of the high-yield mutant strain to the mixture of mineral salt medium and soybean for semi-solid state fermentation to give a fermented product; wherein the ratio of the volume of the high-yield mutant strain to the volume of soybeans in the mixture for inoculation is 5:100-10:100; the ratio of the volume of the mineral salt medium to the volume of soybeans in the mixture is 25:100-35:100; said semi-solid state fermentation is conducted at 30-40° C., 80-90% humidity for 2-3 days.

Step 6: extraction of the crude fermented product to give a yellow precipitate; the extraction method for crude product is comprising of:

A. washing the fermented product with purified water and placing the washed fermented product in a 250 mesh filter bag for solid-liquid separation by using a liquid extracting machine;

B. centrifugation of the separated liquid at 5000 rpm for 15 minutes at 4° C., collecting supernatant and adjusting its pH to 4.0 by using concentrated HCl, followed by centrifugation at 10000 rpm for 30 minutes at 4° C. and collection of the precipitate;

C. re-suspension of the precipitate in a separating funnel containing dichloromethane and separation of the layers by vortex and incubation before collection of the organic layer. Use a rotary vacuum evaporator to evaporate organic solvent to give a yellow precipitate, a crude surfactin.

Step 7: Dissolution of the yellow precipitate in deionized water before filtration with a 0.22 μm membrane filter. Placing the filtrate in cellulose membrane with different molecular weight cut-offs (MWCO) and using a Amicon magnetically stirred ultrafiltration cell for concentration at 3 kg/cm² of pressure. Collection of the filtrate by filtering the content through a 44.5 mm hollow fiber ultrafiltration cartridge under the pressure of $1.7 \times 10^5$ Pa to give a purified surfactin.

Present invention provides a method of semi-solid state fermentation for producing surfactin from a mutant strain of *Bacillus subtilis* subsp and the method can produce surfactin up to 7.11 g/kg.

DETAILED DESCRIPTION OF THE PREFERRED EMBODIMENT

Example 1 Screening for the Mutants of *Bacillus subtilis* Subsp

Activate the *Bacillus subtilis* ssp. isolated from Thailand seawater shrimp ponds with the nutrient broth and treat with 20 μg/ml EtBr at 30° C. for 24 hrs. Inoculate the mutated bacterial culture onto a solid nutrient agar and incubate at 30° C. for 16 hrs. Select single colonies and inoculate the single colonies into mineral salt medium and incubate at 30° C. for 24 hrs before extraction of bacterial RNA. Relative quantification of the sfp gene and the rpo gene is analyzed by using primers (Table 1) and the results are compared with the control group (strains without EtBr treatment) to screen for mutants with high sfp gene expression, which are the high-yield mutant strains of *Bacillus subtilis* subsp. The high-yield mutant strain of *Bacillus subtilis* subsp has been deposited in China General Microbiological Culture Collection Center (CGMCC), on Dec. 31, 2014, with a deposition number CGMCC No. 10270. The address of China General Microbiological Culture Collection Center is NO. 1 West Beichen Road, Chaoyang District, Beijing 100101, China.

TABLE 1

Primers

| Primer | Sequence | Base |
|---|---|---|
| SFP-P1(SEQ ID NO 1) | 5'- AAAAC GGRAG AWAT -3' | 14 |
| SFP-P2(SEQ ID NO 2) | 5'- AARCG RAASC GATMA G -3' | 16 |
| rpoβ-F(SEQ ID NO 3) | 5'- GTGGT TTCTT GATGA GGGTC -3' | 20 |
| rpoβ-R(SEQ ID NO 4) | 5'- GGAAT GACAG TTGCG GTA -3' | 18 |

Example 2 Semi-Solid State Fermentation

Soak the organic soybeans (from U.S.) in water for 16 hrs and cook the soybeans in water that is equivalent to 10% of the volume of soybeans at 121° C. for 30 minutes. Inoculate the bacterial culture of the 10% high-yield mutant strain onto the cooked soybeans after cooling to room temperature and add 30% final volume sterilized water (semi-solid state fermentation), 30% final volume mineral salt medium (semi-solid state fermentation), and no water (solid-state fermentation) separately, mix well, place on a iron plate and covered with gauze and incubate at 30° C., 80% humidity for 48 hrs. Collect the fermented soybeans for analysis every 24 hrs.

Figure 1:
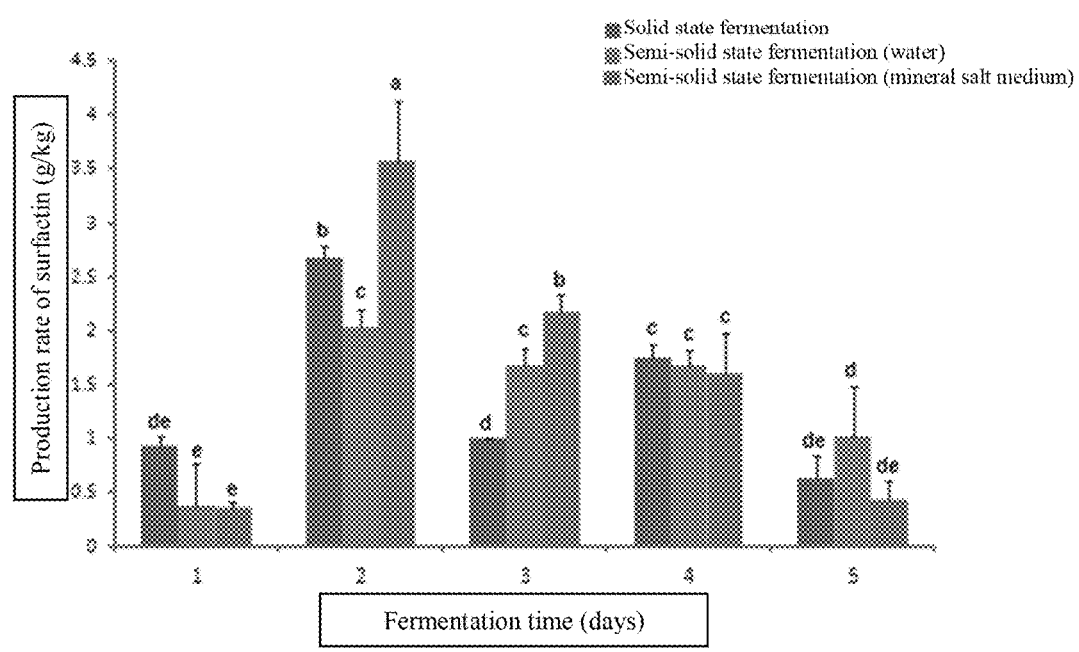
FIG. 1 shows the yield of surfactin by using semi-solid state fermentation and solid-state fermentation.

The results are shown in FIG. 1: mineral salt medium with semi-solid state fermentation gave the best surfactin yield on Day 2 after fermentation when compared with other two groups.

Example 3 Analysis of Crude Surfactin

Dissolve crude surfactin in distilled water and filter with a 0.22 µm filter membrane before subjected to High Performance Liquid Chromatography (HPLC) analysis. Use Techsphere 5 mm ODS C18 reverse column, column temperature: 30° C., mobile phase: 3.8 mM, trifluroacetic acid:acetonitrile=1:4, flow rate: 1 ml/min, wavelength: 210 nm and sample volume: 20 µl (Wei et al., 2003).

Figure 2:
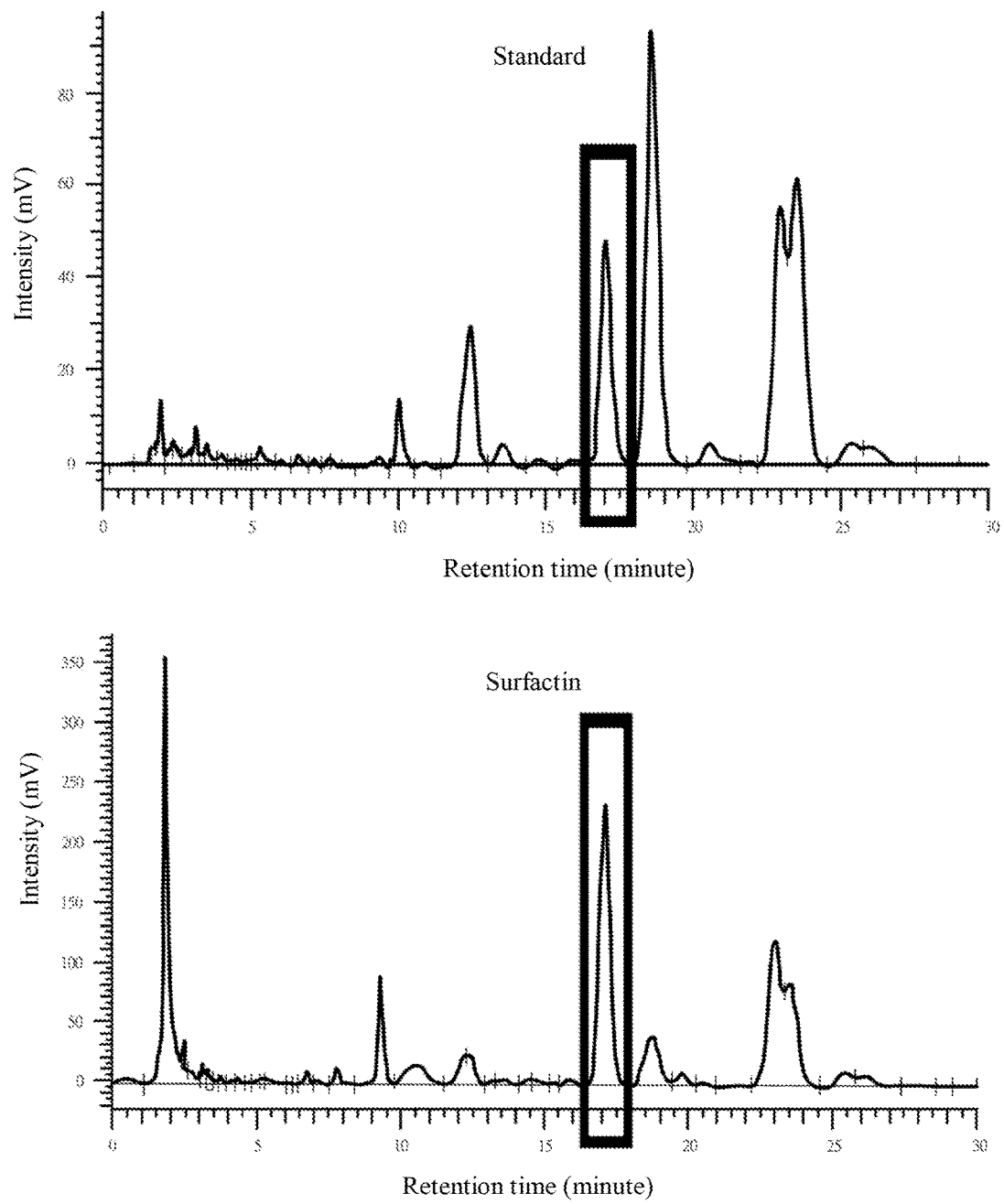
FIG. 2 shows the HPLC chromatograms of the crude surfactin.

Results are shown in FIG. 2: the standard is the commercial standard *Bacillus subtilis* subsp ATCC 21332 (Sigma). The sample is the surfactin produced by the high-yield mutant strain. From previous studies, the 17-min peak molecular weight detected by MALDI-TOF is the closest to the molecular weight of surfactin, 1022 kD and therefore this time point is selected for quantitative and qualitative analysis.

Example 4 Correlation Between the Growth Curve and Surfactin Yield of *Bacillus subtilis* Subsp During the growth phase of the high-yield mutant strain of *Bacillus subtilis* subsp., the culture was collected every 12 hrs for measurement of the absorbance at 600 nm by using a spectrophotometer. For samples with an absorbance higher than 0.7, culture is diluted before being subjected to measurement. In addition, 10 ml of the culture medium is collected every 12 hrs for analysis the surfactin yield by using HPLC.

Figure 3:
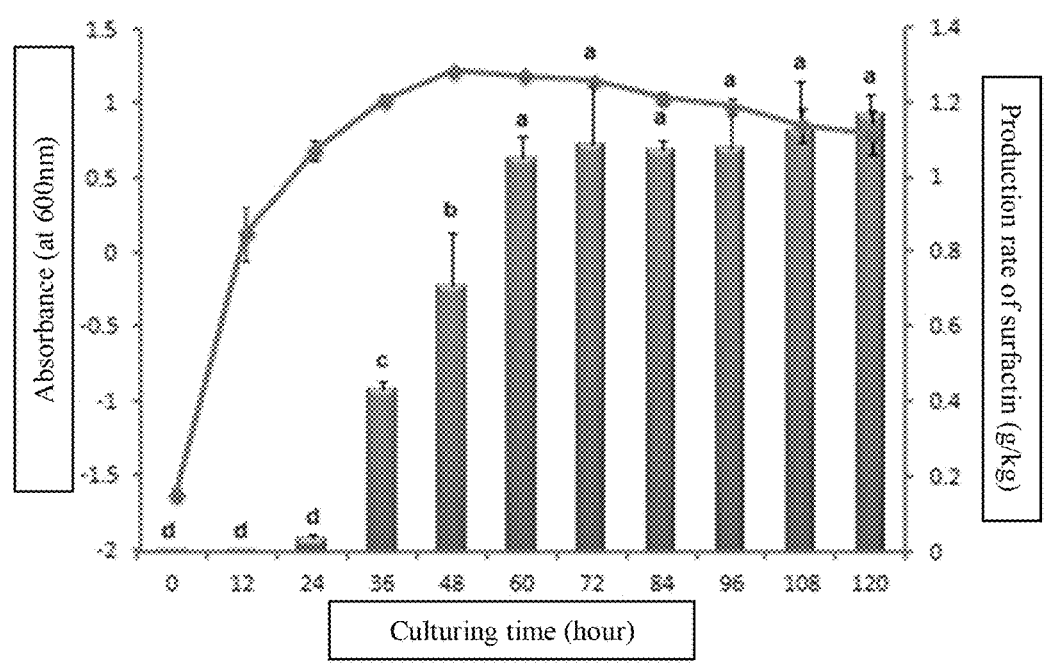
FIG. 3 shows the correlation between the growth curve and surfactin yield of *Bacillus subtilis* subsp.

The results are shown in FIG. 3: The period between 0 and 48 hrs during incubation of the mutant strain of *Bacillus subtilis* subsp. is the logarithmic phase and then bacterial growth enters the stationary phase, whereas surfactin yield starts to increase 24 hrs after incubation and reaches a stable yield after 60 hrs of incubation.

Example 5 Correlation Between Sfp Gene Expression and Surfactin Yield

Culture the mutated single colonies in mineral salt medium at 30° C. for 24 hrs before extraction of bacterial RNA and analysis of relative quantification of sfp gene and rpo gene.

Figure 4:
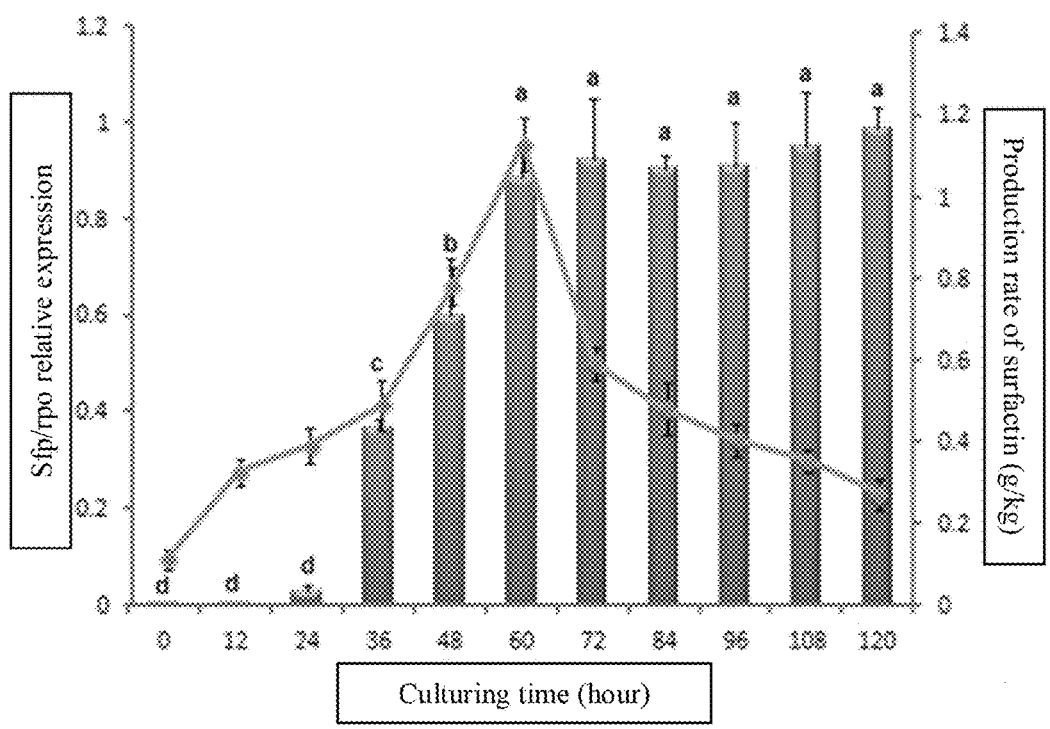
FIG. 4 shows the standards for screening of the high sfp expression clones which are the mutant strains of *Bacillus subtilis* subsp with high surfactin yield.

The results are shown in FIG. 4: those with higher sfp/rpo gene expression also produce more surfactin.

Example 6 Measurements of Surface Tension of Surfactin

Figure 5:
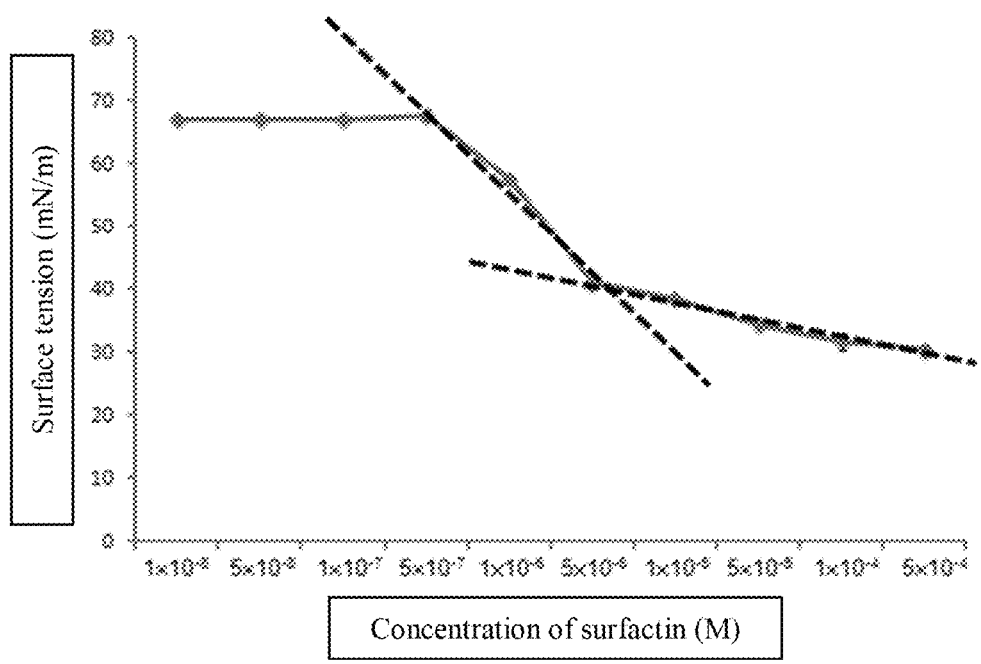
FIG. 5 shows measurements of surface tension of surfactin.

A DST 30 Series Surface Tension Meter is used for measurements of surface tension of surfactin, purified water is used as the control group and its surface tension is 72 mN/m. Perform serial dilution on surfactin: $5\times10^{-4}$ M, $1\times10^{-4}$ M, $5\times10^{-5}$ M, $1\times10^{-5}$ M, $5\times10^{-6}$ M, $1\times10^{-6}$ M, $5\times10^{-7}$ M, $1\times10^{-7}$ M, $5\times10^{-8}$ M and $1\times10^{-8}$ M to give its critical micelle concentration (CMC) and the results are shown in FIG. 5.

Example 7 Measurements of Emulsification Activity of Surfactin

Figure 6:
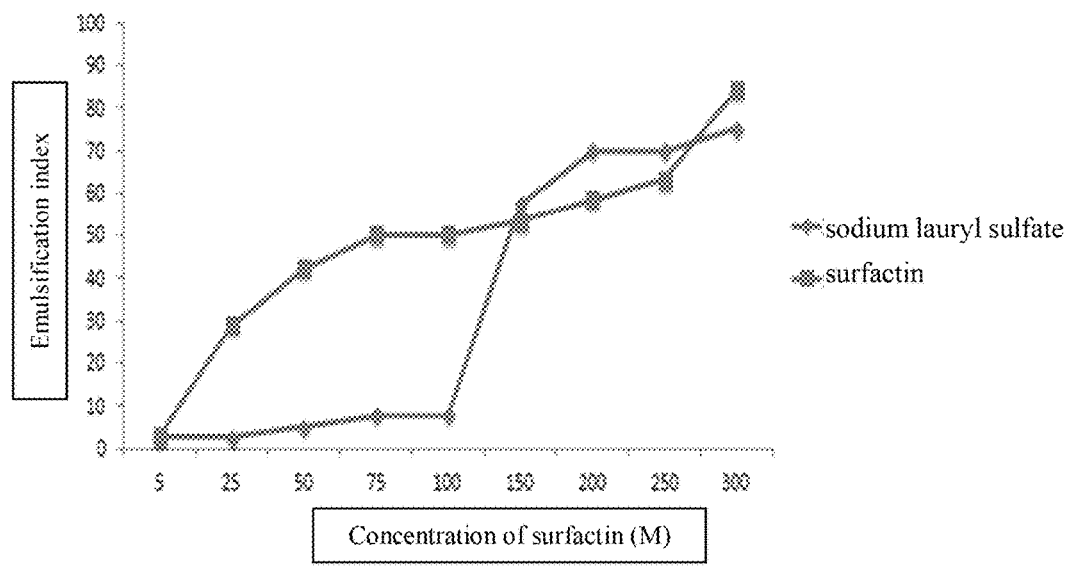
FIG. 6 shows measurements of the emulsification activity of surfactin.

The method used by Cooper et al. is selected: surfactin is dissolved in purified water and prepared in different concentrations, take 2 ml of the diluted surfactin and add 3 ml of kerosene (coal oil) to the test tube, vortex the tube for 2 minutes and incubate at room temperature for 24 hrs. Measure the ratio of the height of the emulsion layer and the total height of the solution and multiply by 100% to give the emulsification index of the test sample. The emulsification activity of oils is represented as emulsification index (E2) and the results are shown in FIG. 6.

Example 8 Antimicrobial Test for Surfactin

*Escherichia coli* DH5α, *Vibrio harveyi*, *Vibrio alginolyticus*, *Vibrio anguillarum*, *Vibrio salmonicida*, *Aeromonas hydrophila* and *Staphylococcus epidermidis* are separately inoculate onto LBA (*E. coli* DH5α) or TSA (+1.5% NaCl) and incubate at 37° C. for 16 hrs. Scrap off and dissolve the colonies in designated medium. When OD540 is at 1 (the concentration is around $1\times10^9$ colonies/c.c.), take 500 µl of the bacterial culture and add to 500 µl of LB or TSB (+1.5% NaCl) to make the bacterial concentration at $1\times10^{4.5}$ colonies/c.c.; add 130 µl of the bacterial culture to each well of a 96-well plate, the concentration of bacterial culture is $1\times10^{4.5}$ colonies/c.c., before addition of 20 µl of chemically synthesized antimicrobial peptides at various concentrations. After 16 hrs of incubation at 37° C., the bacterial culture that is clear indicates the lowest concentration of the antimicrobial peptide, that is, minimum inhibitory concentration (MIC).

Results are shown in Table 2: the minimum inhibitory concentration (MIC) of the surfactin produced by high-yield mutant strain of *Bacillus subtilis* subsp. is 96.5 μM when compared with the surfactin produced by *Bacillus subtilis* subsp. ATCC21332.

TABLE 2

Comparison of the minimum inhibitory concentration (MIC) of the surfactin produced by *Bacillus subtilis* subsp. ATCC21332 and high-yield mutant strain of *Bacillus subtilis* subsp..

|  | *Bacillus subtilis* subsp. ATCC21332 | High-yield mutant strain |
|---|---|---|
| Gram positive | | |
| *E. coli* | 193 | 96.5 |
| *Aeromonas* | 128.7 | 96.5 |
| *vibrio anguillarum* | 128.7 | 96.5 |
| *Vibrio alginolyticus* | 128.7 | 96.5 |
| *Vibrio harveyi* | 128.7 | 96.5 |
| *Vibrio salmonicida* | 128.7 | 96.5 |
| Gram negative | | |
| *Staphylococcus epidermidis* | 128.7 | 96.5 |

What is claimed is:

1. A method of semi-solid state fermentation for producing surfactin from a high-yield mutant strain of *Bacillus subtilis* subsp., wherein the method comprises following steps:
   Step A: inoculate said high-yield mutant strain of *Bacillus subtilis* subsp. to a mixture of mineral salt medium and soybeans for semi-solid state fermentation to give a fermented product, wherein said soybean is whole soybean; and
   Step B: perform extraction of the crude fermented product to give a yellow precipitate;
   Step C: purify said yellow precipitate to give a purified surfactin;
   wherein the deposition number of the high-yield mutation strain of *Bacillus subtilis* subsp. is CGMCC 10270.

2. The method of claim 1, wherein the mineral salt medium disclosed in step A is selected from the group consisting of 2-6% (v/v) glucose, 35-45 mM $Na_2HPO_4$, 25-35 mM $KH_2PO_4$, 45-55 mM $NH_4NO_3$, 5-10 mM $CaCl_2$, 2-6 mM Sodium EDTA, 750-850 mM $MgSO_4.7H_2O$ and 1-3 mM $FeSO_4.7H_2O$.

SEQUENCE LISTING

<160> NUMBER OF SEQ ID NOS: 4

<210> SEQ ID NO 1
<211> LENGTH: 14
<212> TYPE: DNA
<213> ORGANISM: artificial sequence
<220> FEATURE:
<223> OTHER INFORMATION: SFP-P1

<400> SEQUENCE: 1
aaaacggrag awat                14

<210> SEQ ID NO 2
<211> LENGTH: 16
<212> TYPE: DNA
<213> ORGANISM: artificial sequence
<220> FEATURE:
<223> OTHER INFORMATION: SFP-P2

<400> SEQUENCE: 2
aarcgraasc gatmag              16

<210> SEQ ID NO 3
<211> LENGTH: 20
<212> TYPE: DNA
<213> ORGANISM: artificial sequence
<220> FEATURE:
<223> OTHER INFORMATION: rpo(beta)-F

<400> SEQUENCE: 3
gtggtttctt gatgagggtc          20

<210> SEQ ID NO 4
<211> LENGTH: 18
<212> TYPE: DNA
<213> ORGANISM: artificial sequence
<220> FEATURE:
<223> OTHER INFORMATION: rpo(beta)-R

<400> SEQUENCE: 4
ggaatgacag ttgcggta            18

3. The method of claim 1, wherein the higher the sfp expression of a high-yield mutant strain, the higher surfactin yield of the high-yield mutant strain.

4. The method of claim 1, wherein the ratio of the volume of the high-yield mutant strain to the volume of soybeans in the mixture for inoculation is 5:100-10:100.

5. The method of claim 1, wherein the ratio of the volume of the mineral salt medium to the volume of soybeans in the mixture in step A is 25:100-35:100.

6. The method of claim 1, wherein the semi-solid state fermentation is conducted at 30-40° C., humidity 80-90% for 2-3 days.

7. The method of claim 1, wherein extraction of crude product in step B comprises:
- washing the fermented product of step B with purified water for liquid-solid separation;
- centrifugation of the liquid obtained after liquid-solid separation at low temperature, collect the supernatant and subject the supernatant to centrifugation at low temperature to give a precipitate;
- re-suspension of the precipitate in dichloromethane, take the organic layer to give a yellow precipitate.

8. The method of claim 1, wherein the yellow precipitate is a crude surfactin.

9. The method of claim 7, wherein the yellow precipitate is a crude surfactin.

10. The method of claim 1 wherein the purification of step C involves using magnetically stirred ultrafiltration cells and hollow fiber ultrafiltration cartridges for purification.

* * * * *